US00PP10809P

United States Patent [19]

Olesen et al.

[11] Patent Number: Plant 10,809

[45] Date of Patent: Mar. 2, 1999

[54] MINIATURE ROSE PLANT NAMED 'POULDANI'

[75] Inventors: L. Pernille Olesen; Mogens N. Olesen, both of Fredensborg, Denmark

[73] Assignee: Poulsen Roser ApS, Fredensborg, Denmark

[21] Appl. No.: 831,721

[22] Filed: Apr. 1, 1997

[51] Int. Cl.[6] ..... A01H 5/00

[52] U.S. Cl. ..... Plt./7.1

[58] Field of Search ..... Plt./7.1

[56] References Cited

U.S. PATENT DOCUMENTS

P.P. 4,867 7/1982 Moore ..... Plt./7.1

OTHER PUBLICATIONS

UPOV-ROM, 1997 Apr., Plant Variety Database, GTI Jouve Retrieval Software, citation for 'POULdani'.

*Primary Examiner*—Howard J. Locker

[57] ABSTRACT

A new bi-colored miniature rose plant which has abundant flowers and good keepability. The variety successfully propagates from softwood cuttings and is suitable for year round production in commercial glasshouses. This new and distinct variety has shown to be uniform and stable in the resulting generations from such asexual propagation.

2 Drawing Sheets

SUMMARY OF THE INVENTION

The present invention constitutes a new and distinct variety of miniature rose plant which was developed by artificially pollinating an unnamed seedling with an unnamed seedling. The two parents were crossed in the summer of 1993 and the resulting seed was sown in December, 1993 in a controlled glasshouse environment. The new variety is named 'POULdani'.

The objective of the hybridization of this rose variety for commercial greenhouse culture was to create a new and distinct variety with:

1. Uniform and abundant flowers with good keepability;
2. Attractive long lasting foliage and compact growth,
3. Year round flowering under glasshouse conditions;
4. Suitability for production from softwood cuttings in pots; and
5. Durable flowers and foliage which make the variety suitable for distribution in the floral industry.

This combination of qualities was not present in previously available commercial cultivars of this type and distinguish 'POULdani' from all other varieties of which we are aware.

The seeds from the hybridization were planted in a controlled environment and evaluations were conducted on the resulting rose plants. 'POULdani' was selected by L. Pernille and Mogens N. Olesen in their rose development program in Fredensborg, Denmark in June of 1994.

Asexual reproduction of 'POULdani' by cuttings and by traditional budding was first done by L. Pernille and Mogens N. Olesen in August of 1994. This initial and subsequent propagations have demonstrated that the characteristics of 'POULdani' are true to type and are transmitted from one generation to the next.

BRIEF DESCRIPTION OF THE DRAWINGS

The accompanying color illustrations show as true as is reasonably possible to obtain in color photographs of this type, the typical characteristics of the buds, flowers, leaves, stems, and a plant of 'POULdani'. Specifically illustrated in sheet 1:

1. Stem or entire plant showing branching and the attachment of leaves, buds, and peduncles;
2. Flower bud, partially opened bud, and open bloom;
3. Flower petals, detached;
4. Sepals, receptacle, and pedicel;
5. Flowering stem, as well as a stem exhibiting thorns; and
6. Leaves.

Specifically illustrated in sheet 2 is an entire blooming plant in a 10 cm pot.

DETAILED DESCRIPTION OF THE VARIETY

The following is a detailed description of 'POULdani', as observed in its growth in glasshouses in Fredensborg, Denmark and in Half Moon Bay, Calif. and in field nursery in Applegate, Oreg. Descriptions were made from plants treated with growth regulators normally used in the greenhouse production process. The growth regulator Paclobutrazol was applied at 30 ppm weekly for three weeks beginning at a plant age of 8 weeks. The peduncle lengths mentioned may actually be shorter and the foliage color several shades darker than on untreated specimens. Color references are made using The Royal Horticultural Society (London, England) Colour Chart, 1995.

Parents: Unnamed seedling and an unnamed seedling.
Classification:
*Botanical.*—Rosa hybrida.
*Commercial.*—Miniature.

Flower and Flower Bud

Blooming cycle: Recurrent.
Flower bud:
*Size.*—10–12 mm in length when petals are just beginning to crack open.
*Bud form.*—Ovoid.
*Bud color.*—Striped. 57 A of the Red-Purple Group and 155 B of the White Group as petals begin to unfurl.

*Sepals.*—R.H.S. 146 B of the Yellow-Green Group. Foliaceous appendages on three of the five sepals. These sepals can be longer than the others with feather-like appendages on the ends. Surfaces of sepals lightly pubescent.

*Peduncle.*—Surface: Smooth. Glabrous. Length: 15–35 mm average length. Color: R.H.S. 144 B of the Yellow-Green Group. Prickles: Few. Strength: Stiff, erect, slender.

*Receptacle.*—Surface: Smooth. Glabrous. Shape: Urn shaped. Size: Small 4 mm×4 mm. Color: R.H.S. 144 A of the Yellow-Green Group.

*Borne.*—Commonly 2–4 buds per flowering stem.

Flower bloom:

*Diameter.*—Small. 30–35 mm. on average.

*Form.*—Upon opening, ovoid to globular. Completely open, form of top of flower is a flattened convex.

*Petalage.*—Double. Average range: 35 petals.

*Color.*—Novel striped coloration. Upon opening, the upper surface of the petal is R.H.S. 57 A of the Red-Purple Group and 155 B of the White Group. After opening, the upper surface of the petal fades slightly to R.H.S. 57 B of the Red-Purple Group and 155 B of the White Group. After flower is open 5–7 days, color on petal fades to 57 C. The reverse side of the petal is R.H.S. 57 C of the Red-Purple Group and R.H.S. 155 B of the White Group. Petal lacks basal spot.

*Reflex.*—Exterior petals are double reflexed. Interior petals can also be double reflexed.

*Fragrance.*—Very light to light.

*Duration.*—8–10 days as a cut flower and 11–14 days on the plant.

Reproductive organs:

*Pollen.*—Yellow Group 138. Present.

*Anthers.*—Regularly located around base. Abundant. Size: Medium. Color: Yellow Group 138.

*Filaments.*—Color: Green-White Group 157A.

*Stigmas.*—Superior in location to anthers.

*Styles.*—Color: Green-White Group 157A.

Plant

Plant growth: Bushy, vigorous, and compact. When grown as a 10 cm pot plant, the average height of the plant itself is 15–18 cm and the average width is 18–22 cm. When grown as a nursery plant on its own roots the average plant height is 30—35 cm and the average plant width is 30–35 cm.

Stems:

*Color.*—Young wood: Between Green Group 139C and Green Group 139D. Older wood: Green. R.H.S. 144 A of the Yellow-Green Group.

*Thorns.*—Incidence: Few thorns. Size: Average length: 2.5–3 mm. Color: Red Group 36B.

Plant foliage: Normal number of leaflets on average leaves: 5–7 leaflets, with the most basal pair being significantly smaller.

*Leaf size.*—Small. 70 mm×45mm.

*Abundance.*—Average.

*Color, mature foliage.*—Upper leaf surface: Medium dark green. R.H.S. 146 A to R.H.S. 146 B of the Yellow-Green Group. Lower leaf surface: Medium green. R.H.S. 147 C of the Yellow-Green Group.

*Color, juvenile foliage.*—Upper leaf surface: Yellow-Green Group 146A. Lower leaf surface: Yellow-Green Group 146C.

Plant leaves and leaflets:

*Stipules.*—Present. 8–10 mm long. Margins are lightly serrated and have a limited number of stiff hairs.

*Petiole rachis.*—Color: Yellow-Green Group 147 B. Underneath: With prickles on leaves with 7 leaflets.

*Edge.*—Serrated.

*Shape.*—Leaflets are Ovate.

*Leaflets.*—Number: 5–7 leaflets, with the most basal pair being significantly smaller.

*Other.*—Semi-glossy finish. Thin texture.

Disease resistance: Resistant to rust, mildew, black spot, and Botrytis under normal growing conditions.

We claim:

1. A new and distinct variety of rose plant of the miniature class, substantially as herein illustrated and described, as a distinct and novel rose variety due to its abundant uniquely striped flowers with good keepability, attractive long lasting foliage and compact growth, year round flowering under glasshouse conditions, suitability for production from softwood cuttings in pots, and durable flowers and foliage which make the variety suitable for distribution in the floral industry.

* * * * *

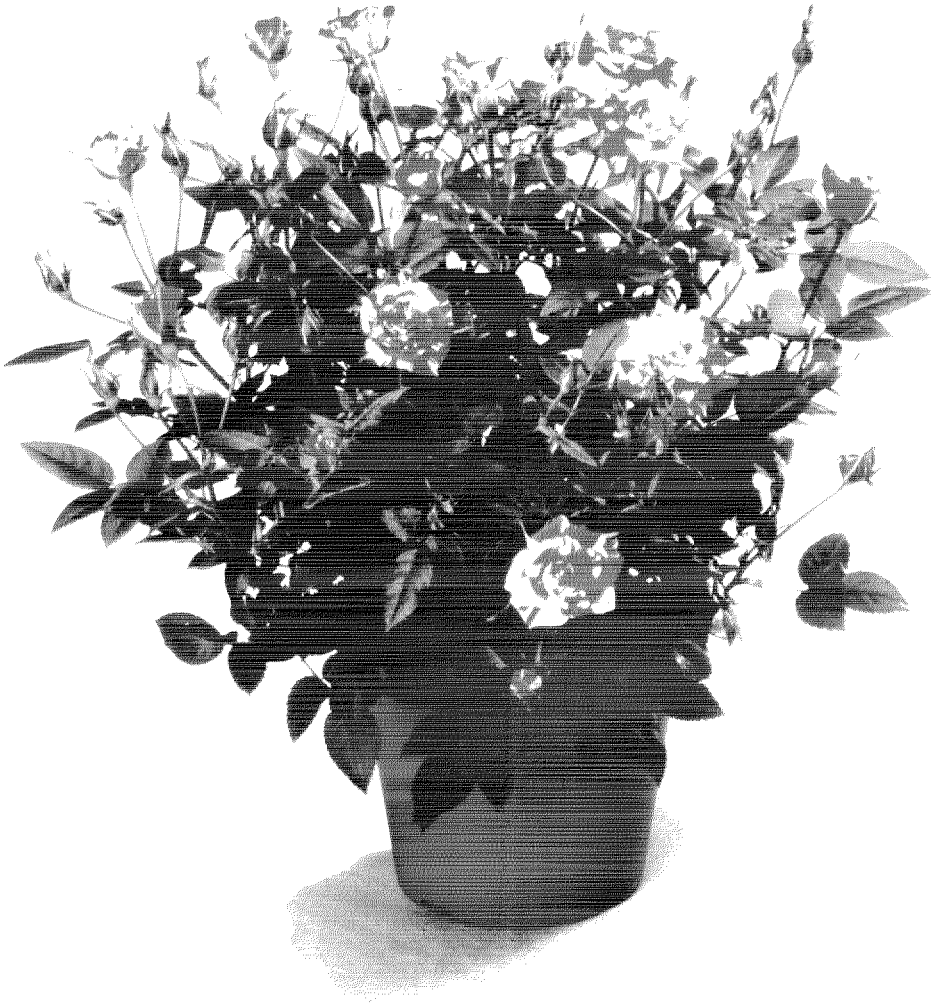

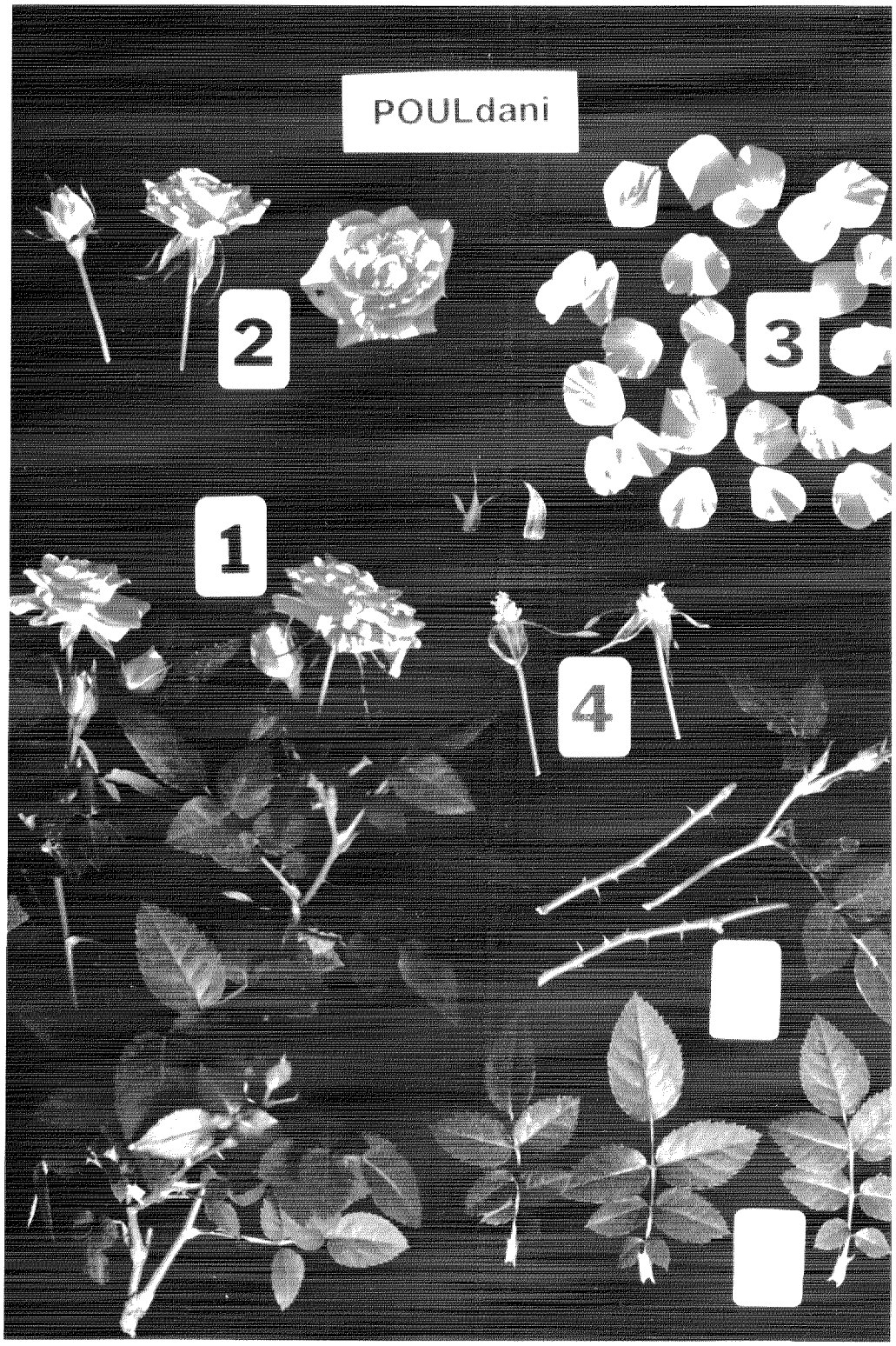
POULdani
2
3
1
4